United States Patent
Behzadi

(10) Patent No.: US 11,103,354 B2
(45) Date of Patent: Aug. 31, 2021

(54) MECHANICAL ASSEMBLY INCLUDING EXTERIOR SURFACE PREPARATION

(71) Applicant: Kambiz Behzadi, Pleasanton, CA (US)

(72) Inventor: Kambiz Behzadi, Pleasanton, CA (US)

(*) Notice: Subject to any disclaimer, the term of this patent is extended or adjusted under 35 U.S.C. 154(b) by 55 days.

(21) Appl. No.: 16/267,813

(22) Filed: Feb. 5, 2019

(65) Prior Publication Data

US 2019/0336294 A1    Nov. 7, 2019

Related U.S. Application Data

(62) Division of application No. 15/234,927, filed on Aug. 11, 2016, now Pat. No. 10,864,083.

(60) Provisional application No. 62/319,377, filed on Apr. 7, 2016.

(51) Int. Cl.
*A61F 2/34* (2006.01)
*B33Y 10/00* (2015.01)
*A61F 2/30* (2006.01)
*A61F 2/46* (2006.01)

(52) U.S. Cl.
CPC ............... *A61F 2/34* (2013.01); *B33Y 10/00* (2014.12); *A61F 2/30965* (2013.01); *A61F 2/4609* (2013.01); *A61F 2002/30014* (2013.01); *A61F 2002/3092* (2013.01); *A61F 2002/30904* (2013.01); *A61F 2002/30985* (2013.01); *A61F 2002/342* (2013.01); *A61F 2002/3417* (2013.01); *A61F 2002/3425* (2013.01); *A61F 2002/4681* (2013.01)

(58) Field of Classification Search
CPC ............ A61F 2/34; A61F 2/30767; A61F 2002/30014; A61F 2002/30904; A61F 2002/3417; A61F 2002/342; A61F 2002/3425; A61F 2002/30841; A61F 2002/30878; A61F 2002/30881; A61F 2002/30897
See application file for complete search history.

(56) References Cited

U.S. PATENT DOCUMENTS

| | | | |
|---|---|---|---|
| 4,608,053 A | 8/1986 | Keller | |
| 5,358,532 A * | 10/1994 | Evans | A61F 2/34 623/22.23 |
| 5,702,473 A | 12/1997 | Albrektsson et al. | |
| 5,713,901 A | 2/1998 | Tock | |

(Continued)

FOREIGN PATENT DOCUMENTS

WO    2007096476 A2    8/2007

OTHER PUBLICATIONS

PCT International Search Report for International application No. PCT/US17/26417, dated Jul. 3, 2017.

(Continued)

*Primary Examiner* — Brian A Dukert
(74) *Attorney, Agent, or Firm* — Patent Law Offices Michael E. Woods; Michael E. Woods

(57) ABSTRACT

A system and method for further improving upon an ability of a surgeon to reduce or eliminate impaction forces when installing or assembling a prosthesis. An implant includes a surface treatment for aiding operations with the implant. For example, some surface treatments provide an asymmetry in installation versus removal to bias the associated implant deeper into an installation site.

7 Claims, 8 Drawing Sheets

(56) References Cited

U.S. PATENT DOCUMENTS

| | | | | |
|---|---|---|---|---|
| 6,146,425 | A | * | 11/2000 | Hoermansdoerfer ..... A61F 2/34 623/22.31 |
| 6,231,612 | B1 | | 5/2001 | Balay et al. |
| 7,875,083 | B2 | | 1/2011 | Sudmann |
| 2014/0012391 | A1 | | 1/2014 | Gugler et al. |
| 2014/0058526 | A1 | * | 2/2014 | Meridew ................ A61L 27/56 623/23.5 |
| 2014/0303743 | A1 | | 10/2014 | Choudhury et al. |
| 2014/0371897 | A1 | | 12/2014 | Lin et al. |
| 2017/0290666 | A1 | | 10/2017 | Behzadi |
| 2017/0290667 | A1 | | 10/2017 | Behzadi |
| 2017/0340448 | A1 | | 11/2017 | Behzadi |

OTHER PUBLICATIONS

PCT Written Opinion of the International Searching Authority for International application No. PCT/US17/26417 dated Jul. 3, 2017.

* cited by examiner

MECHANICAL ASSEMBLY INCLUDING EXTERIOR SURFACE PREPARATION

CROSS REFERENCE TO RELATED APPLICATIONS

This application is a division of U.S. patent application Ser. No. 15/234,927 filed 11 Aug. 2016 which claims benefit of U.S. Patent Application No. 62/319,377 filed 7 Apr. 2016 and also is related generally to U.S. Patent Application No. 61/921,528 filed 29 Dec. 2013, to U.S. Patent Application No. 61/980,188 filed 16 Apr. 2013, U.S. patent application Ser. No. 14/584,656 filed 29 Dec. 2014 (now U.S. Pat. No. 9,168,154), to U.S. patent application Ser. No. 14/585,056 filed 29 Dec. 2014 (now U.S. Pat. No. 9,220,612), to U.S. patent application Ser. No. 14/923,203 filed 26 Oct. 2015, to U.S. patent application Ser. No. 14/969,721 filed 15 Dec. 2015, to U.S. Patent Application No. 62/277,294 filed 11 Jan. 2016, to U.S. patent application Ser. No. 14/965,851 filed 10 Dec. 2015, to U.S. patent application Ser. No. 15/055,942 filed 29 Feb. 2016, and to U.S. patent application Ser. No. 15/092,384 filed 6 Apr. 2016, all the contents of which are all hereby expressly incorporated in their entireties by reference thereto for all purposes.

FIELD OF THE INVENTION

The present invention relates generally to mechanical assembly and assemblies, and more specifically, but not exclusively, to a prosthesis including its construction, assembly, and installation.

BACKGROUND OF THE INVENTION

The subject matter discussed in the background section should not be assumed to be prior art merely because of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

The incorporated patents and applications often address a problem of applied forces in the assembly and installation of mechanical systems, such as a prosthesis used in orthopedic surgery.

There are many considerations regarding the use of applied impact forces in orthopedic surgery and in particular the use of a hammer or a mallet to apply an impact force. Much work has been done to help understand, control, modulate, and replace the impaction forces created by the surgeon's mallet. Some of the incorporated references have described various components of these applied forces, often using orthopedics as an example though the invention is not required to be so limited. The use of a mallet in orthopedics creates a momentum or an impulse and effects of the impulse in creating an impaction force can be broken down into its components, including magnitude, frequency and dwell time. Some of the incorporated references include systems and methods of substituting an installation force for the impaction force in orthopedic surgery. Embodiments of the incorporated references may allow the surgeon to perform some of these surgeries in a safer and more controlled fashion by rethinking conventional procedures related to a prosthesis. Further, some of the incorporated references relate to assembly of a prosthesis for use in an orthopedic procedure.

The collection of incorporated references includes multiple embodiments of multiple inventions, with some of these embodiments including a use of vibratory force/energy that disclosed as important for addressing problems with application of impaction forces.

In some of the embodiments of the incorporated patents and applications, there is a discussion that there may be significant advantage to use of controlled installation forces communicated to a prosthesis or prosthesis component at higher (including ultrasonic) frequencies. Some or a significant portion of these advantages may relate to differences between kinetic and static coefficients of friction, and/or vibratory modes of the installation site (bone) or mating component for a prosthetic assembly, among other possible explanations. These features may allow a prosthesis (or portion thereof) vibrating at an appropriate mode to diminish, sometimes significantly, forces resisting installation or assembly, respectively. With these diminished forces, the surgeon may be able to employ decreased installation forces which allow easier and safer insertions. In some embodiments, the embodiment may allow for a concurrent ability to align the prosthesis during/after installation as part of the same procedure with the same tools. This contrasts with conventional systems which employ one set of tools for insertion and then another set of tools after insertion to correction malpositioning. Some embodiments of the present invention may allow for concurrent insertion and desired positioning.

Current surface treatment of a prosthesis is designed for porous metal ingrowth bonding of a prosthesis to bone (in contrast to a use of cement to bond a prosthesis to bone). In general, the porous implants are typically created as "composite structures" consisting of a substrate typically made of either cobalt chrome or titanium alloy (which carries the patient's weight), and a porous surface which is designed to enhance osseointegration of the implant (referred to as "porous coating"). The porous coating includes microstructural features such as peaks, valleys and deep caves. This mimics the structure of trabecular/cancellous bone with its three-dimensional and interconnecting network of pores and capillary properties. The porous coating aids in initial scratch fixation as well as long term fixation through osseointegration of bone with the surface of the bone. Recently, there have been many advances in the creation of the porous coating that more accurately resemble the trabecular bone. These techniques all involve multiple steps in the creation of the porous coating surface and subsequent bonding of this surface to the alloy substrate. Today, the majority of porous coatings are made of titanium or tantalum. These porous coatings are textured with desirable mechanical properties closer to bone and with desirable porosity. They are created separately and applied to the actual implant (as a composite structure) via variety of bonding methods including plasma spray, chemical etching thin films and plates, chemical and/or physical vapor disposition, sintering, brazing, diffusion bonding, gluing or cementing, and the like). Thus, the porous coating that is seen on the surface of a typical conventional prosthesis is: i) a composite structure that must to be added to the substrate, and ii) a randomized pattern with no preferential orientation and or design.

Fixation of hip and knee replacement implants to bone is critical to the success of the procedure. A variety of roughened surfaces and three-dimensional (3-D) porous surfaces have been used to enhance biological fixation on orthopedic implants for over 30 years. More recently, highly porous metals have emerged as versatile biomaterials that may enhance fixation to bone and are suitable to several applications in hip and knee replacement surgery. The advantages provided by these newly developed porous metals may improve cementless fixation and long-term patient outcomes in hip and knee replacement.

Thermal spray technologies involving the melting and subsequent spraying of metal feedstock have been leveraged by various implant manufacturers to apply highly roughened commercially pure titanium (CPTi) and titanium (Ti) alloy coatings onto implants used in hip and knee arthroplasty. These include: wire arc deposition, plasma spray, sintering porous beads, diffusion bonding of titanium coatings, advanced highly porous coating technologies using tantalum and titanium, among other procedures.

Current installation procedures for some prosthesis, such as for an acetabular cup, include attachment of a rod axially aligned with a longitudinal axis of the prosthesis that is used to apply the impacting forces and impact the prosthesis into the bone to the desired depth.

What is needed is a system and method for further improving upon an ability of a surgeon to reduce or eliminate impaction forces when installing or assembling a prosthesis.

BRIEF SUMMARY OF THE INVENTION

Disclosed is a system and method for improving upon an ability of a surgeon to reduce or eliminate impaction forces when installing or assembling a prosthesis.

The following summary of the invention is provided to facilitate an understanding of some of the technical features related to surface treatment for mating/contacting surfaces of a prosthesis or a prosthesis component, and is not intended to be a full description of the present invention. A full appreciation of the various aspects of the invention can be gained by taking the entire specification, claims, drawings, and abstract as a whole. The present invention is applicable to other prosthesis devices in addition to acetabular cups, to other mechanical systems for reduced force insertion of one structure into another, and to other configurations and arrangements of exterior surface structures than those presented or described herein.

In an embodiment of the present invention, an implant may include a surface treatment for aiding operations with the implant. For example, some surface treatments provide an asymmetry in installation versus removal to bias the associated implant deeper into an installation site.

An embodiment of the present invention includes a surface treatment, whether produced as an innate outer surface feature of the device during manufacture or added to a surface (e.g., an outer surface) of a device, such as, for example, a retrofit solution. The surface treatment provides an asymmetric relative force for the device in cooperation with material of an installation side (e.g., easier to push the prosthesis into a bone than to extract the prosthesis from the bone). For example, the treatment includes provision of various exterior structures that interact with material of the installation site more strongly in one relative direction (e.g., removal or disassembly from the installation site) than in another direction (e.g., insertion or assembly into the installation site). For example, the surface treatment of the prosthesis collectively offers less resistance to installation than removal.

An embodiment of the present invention may provide for both asymmetric relative forces while also including enough randomization for porous ingrowth of bone for post-installation bonding enhancement. The surface treatment and/or the ingrowth structures may be microscopic and/or macroscopic.

An embodiment of the present invention may include exterior surface structures and configurations that provide an acute angle relative to an insertion path. For example, when installing an acetabular cup into a prepared installation site of an acetabulum, the cup follows a path as it is inserted into the desired location and depth. Exterior surface portions of the cup are in contact with, and move past, the bone of the walls of the installation site. For one type of surface treatment, exterior surface structures of the surface treatment could be angled relative to the walls. The angles could be angled acutely forward (e.g., towards a bottom of the installation site) which may increase installation forces and decrease removal forces, angled perpendicularly which may be neutral as to directionally, and/or angled backward (e.g., away from the bottom of the installation site) which may increase removal forces and decrease installation forces. The magnitude, and differences, of these asymmetric forces may be influenced by many different factors including materials of the exterior surface elements and complementary material of the contacting surfaces of the installation site, characteristic size and arrangement of the exterior surface elements, design goals, and/or intended use.

An embodiment of the present invention may include exterior surface structures and configurations that provide pitched structures, relative to an insertion path, that vary over the surface that provide for asymmetric relative installation forces.

An embodiment of the present invention may include a specially configured exterior surface to present a two-dimensional or a three-dimensional variable stiffness that is more conducive for transmission of force and energy longitudinally (e.g., parallel to the insertion path) and less conducive to circumferential transmission (e.g., perpendicular to the insertion path). That is, there is an asymmetry of the structural response of the surface treatment to make it easier to move along the path while retaining the circumferential integrity for being held in place once installed.

An embodiment of the present invention may include use of additive manufacturing techniques to produce a final prosthesis having an integrated surface treatment that may not require a multi-step process of applying a porous surface treatment to an underlying prosthetic foundation.

An embodiment of the present invention may include use of subtractive manufacturing techniques to produce a final prosthesis having an integrated surface treatment that may not require a multi-step process of applying a porous surface treatment to an underlying prosthetic foundation.

An embodiment of the present invention may include a different installation adaptor for applying forces used to locate a prosthesis within a bone. The conventional method of using an apex-attached rod to apply the forces may be thought of as "pulling" the prosthesis through the installation site. In contrast, an embodiment may include an attachment modality or adaptor that operates on the perimeter and/or inside surfaces to push the prosthesis through the bone. These embodiments may implicate other embodiments regarding 2D/3D wall configuration for interacting the prosthesis with the installation site.

Any embodiment of the present invention may be superior through manipulation of the friction between contacting surfaces of the prosthesis relative to the material of the installation site. The BMD3 vibratory mechanism may contribute to shifting some or all of the frictional forces from a static coefficient of friction regime to a kinetic coefficient of friction regime. Other factors may also be contributing to a reduction in installation forces required. Similarly, some of the effects of the surface treatment and/or surface application may implicate, at least partially, a transformation of some or all of the resistive forces into the kinetic coefficient of friction regime.

Any of the embodiments described herein may be used alone or together with one another in any combination. Inventions encompassed within this specification may also include embodiments that are only partially mentioned or alluded to or are not mentioned or alluded to at all in this summary or in the abstract. Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

An embodiment of the present invention may be adapted for impact installation and is not limited to other non-impactful installation procedures which may reduce a magnitude of the impact force needed and which may reduce risks of shattering bone at the installation site.

An embodiment of the present invention may include a cream, paste, gel, or other substance that may be applied to contacting surfaces of a prosthesis to be forced into an installation site. This surface treatment may function similar to a lubricant or "shaving cream" to allow to contacting surfaces to more easily move past each other and reduce a magnitude of forces used for an installation. This surface treatment may be combined with other disclosed embodiments and may be dynamically applied as the prosthesis is about to be installed at the installation site.

A method for producing a prosthesis for an installation of the prosthesis into a relatively undersized cavity, the relatively undersized cavity providing a resistive force for installation of the prosthesis into the relatively undersized cavity, including a) manufacturing additively a structure for the prosthesis, the structure including a foundation and a surface; and b) during the manufacturing step a) establishing one or more portions of the structure configured to produce an increased propensity for insertion of the prosthesis into the relatively undersized cavity during the installation, the propensity for insertion responsive to a set of exterior surface structures that extend, relative to an insertion path, that include a pitch having a monotonic varying spacing over the surface parallel to the insertion path, the pitch providing for a set of asymmetric relative installation forces.

An embodiment of the present invention may include use of the disclosed embodiments and implementations for assembling a prosthesis (inserting one component of a modular prosthesis into a mating receptacle of another component of the modular prosthesis).

Other features, benefits, and advantages of the present invention will be apparent upon a review of the present disclosure, including the specification, drawings, and claims.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, explain the principles of the present invention.

DETAILED DESCRIPTION OF THE INVENTION

Figure 1:
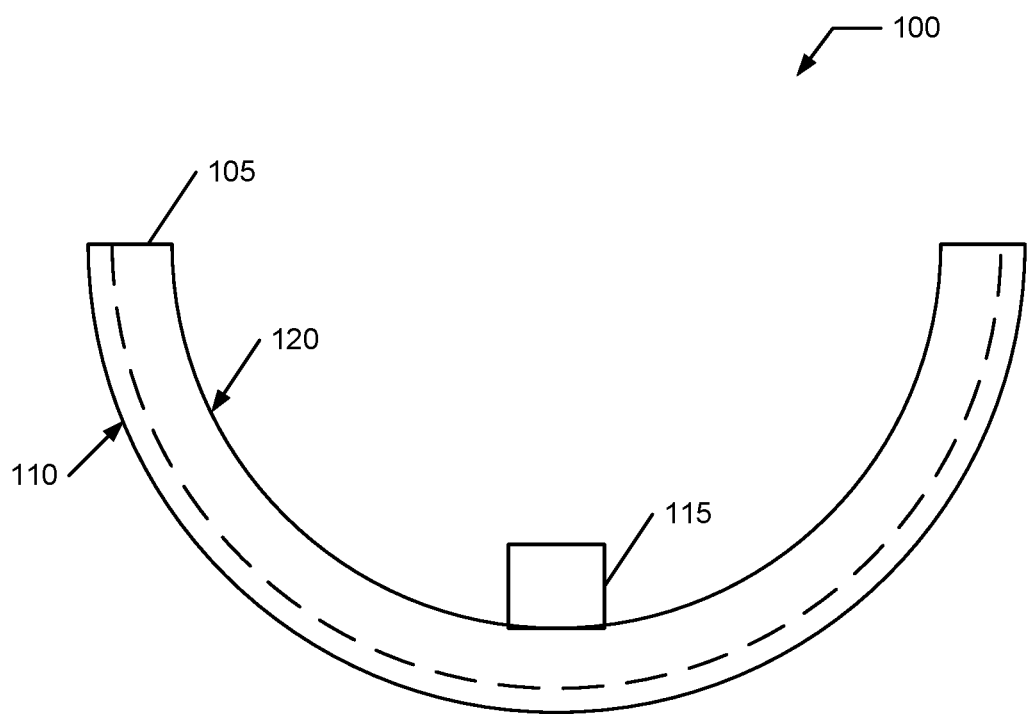
FIG. 1 illustrates a sectional side view of an embodiment of the present invention.

Embodiments of the present invention provide a system and method for further improving upon an ability of a surgeon to reduce or eliminate impaction forces when installing or assembling a prosthesis. The following description is presented to enable one of ordinary skill in the art to make and use the invention and is provided in the context of a patent application and its requirements.

Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Definitions

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The following definitions apply to some of the aspects described with respect to some embodiments of the invention. These definitions may likewise be expanded upon herein.

As used herein, the term "or" includes "and/or" and the term "and/or" includes any and all combinations of one or more of the associated listed items. Expressions such as "at least one of," when preceding a list of elements, modify the entire list of elements and do not modify the individual elements of the list.

As used herein, the singular terms "a," "an," and "the" include plural referents unless the context clearly dictates otherwise. Thus, for example, reference to an object can include multiple objects unless the context clearly dictates otherwise.

Also, as used in the description herein and throughout the claims that follow, the meaning of "in" includes "in" and "on" unless the context clearly dictates otherwise. It will be understood that when an element is referred to as being "on" another element, it can be directly on the other element or intervening elements may be present therebetween. In contrast, when an element is referred to as being "directly on" another element, there are no intervening elements present.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common properties.

As used herein, the term "adjacent" refers to being near or adjoining. Adjacent objects can be spaced apart from one another or can be in actual or direct contact with one another. In some instances, adjacent objects can be coupled to one another or can be formed integrally with one another.

As used herein, the terms "connect," "connected," and "connecting" refer to a direct attachment or link. Connected objects have no or no substantial intermediary object or set of objects, as the context indicates.

As used herein, the terms "couple," "coupled," and "coupling" refer to an operational connection or linking. Coupled objects can be directly connected to one another or can be indirectly connected to one another, such as via an intermediary set of objects.

The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of ±10 percent of the given numeric value provided such a deviation does not alter the end function or result of the value. Therefore, a value of about 1% can be construed to be a range from 0.9% to 1.1%.

As used herein, the terms "substantially" and "substantial" refer to a considerable degree or extent. When used in conjunction with an event or circumstance, the terms can refer to instances in which the event or circumstance occurs precisely as well as instances in which the event or circumstance occurs to a close approximation, such as accounting for typical tolerance levels or variability of the embodiments described herein.

As used herein, the terms "optional" and "optionally" mean that the subsequently described event or circumstance may or may not occur and that the description includes instances where the event or circumstance occurs and instances in which it does not.

As used herein, the term "size" refers to a characteristic dimension of an object. Thus, for example, a size of an object that is spherical can refer to a diameter of the object. In the case of an object that is non-spherical, a size of the non-spherical object can refer to a diameter of a corresponding spherical object, where the corresponding spherical object exhibits or has a particular set of derivable or measurable properties that are substantially the same as those of the non-spherical object. Thus, for example, a size of a non-spherical object can refer to a diameter of a corresponding spherical object that exhibits light scattering or other properties that are substantially the same as those of the non-spherical object. Alternatively, or in conjunction, a size of a non-spherical object can refer to an average of various orthogonal dimensions of the object. Thus, for example, a size of an object that is a spheroidal can refer to an average of a major axis and a minor axis of the object. When referring to a set of objects as having a particular size, it is contemplated that the objects can have a distribution of sizes around the particular size. Thus, as used herein, a size of a set of objects can refer to a typical size of a distribution of sizes, such as an average size, a median size, or a peak size.

FIG. 1 illustrates a sectional side view of an embodiment of the present invention represented using a prosthesis 100 including a foundation portion 105 and an exterior contacting portion 110. In some cases, prosthesis 100 may include an optional mounting structure 115 attached to, or integrated with, an interior wall 120.

Prosthesis 100 in FIG. 1 is an acetabular cup used in total hip replacement medical procedures. Prosthesis 100 is installed into a prepared installation site of an acetabulum that defines a reamed socket in a portion of bone of an acetabulum that is about equal to a diameter of the acetabular cup. When installed, exterior contacting portion 110 contacts the bone portion of the installation site. Installation of an acetabular cup requires that it be forced into the installation site while exterior contacting portion 110 is engaged, in varying degrees, with the living bone. Some of the disclosed embodiments provide materials, configuration, arrangement, and orientation of surface elements defined by exterior contacting portion 110 that provide, collectively, an overall asymmetric force with respect to one or more of the contacted portions of the bone portion. In this context, asymmetric force means that engagement forces between the bone portion and prosthesis 100 have a magnitude in one direction of motion (e.g. deeper into the installation) as compared to another direction (e.g., removal from the installation site) that are different. For example, contacting portion 110 may result in installation forces with respect to the installation site that are less than removal forces from the installation site once installed. Other directions and other asymmetries are possible that for some embodiment it may be desirable to have installation forces be greater than removal forces. A magnitude of the asymmetry may be determined by different factors appropriate for a particular embodiment.

Prosthesis 100 depicted as including at least two portions: foundation portion 105 and exterior contacting portion 110 which is not meant to imply any particular manufacturing process, configuration, or arrangement beyond the presence of two functional portions.

Foundation portion 105 may be thought of as providing structural integrity and strength for weight-bearing and loading, and support for exterior contacting portion 110. Exterior contacting portion 110 defines the surface elements that produce aggregate asymmetric forces during contacted motion with bone of the installation site.

Foundation portion 105 and exterior contacting portion 110 may be formed in many ways. As illustrated in FIG. 1, exterior contacting portion 110 is integrally produced with foundation portion 105 during manufacturing of prosthesis 100. For example, additive manufacturing techniques may be used to define the different portions at different points during the manufacturing. Three-dimensional (3D) printing is a representative class of additive manufacturing equipment that may be used to seamlessly produce prosthesis 100 with exterior contacting portion 110 seamlessly integrated with foundation portion 105.

In other embodiments, prosthesis 100 may be produced using a two-step process in which foundation portion 105 is manufactured first and then in a separate manufacturing process exterior contacting portion 110 is added onto desired surfaces of foundation portion 105 to produce prosthesis 100. In some cases, exterior contacting portion 110 may be produced first as a template and then foundation portion added later.

For purposes of this invention, the term "surface treatment" is used to include all these implementations of exterior contacting portion 110. This term is not limited to any particular arrangement or configuration of exterior contacting portion 110.

As noted herein, one desirable feature of current prosthetic implants includes a surface arrangement for a randomized exterior that includes pores/cavities/voids of a particular characteristic that are used to promote bone ingrowth for bonding prosthesis 100 at the installation site. Some configurations of exterior contacting portion 110 may be configured with such in-growth bonding features implemented consistent with the manufacturing technique for prosthesis 100. The surface treatment itself may include a microscopic and/or a macroscopic characteristic dimension for the implementing structural elements.

For example, with the use of additive manufacturing, the set of instructions for forming prosthesis 100 result from a set of instructions executed by the additive manufacturing equipment. That set of instructions may be defined by various 3D design tools and various mathematical instructions. Those instructions may include a superposition of asymmetric structural elements and randomized void-definition processes such that exterior contacting portion 110 includes both characteristics. In other embodiments, void-definition processes may be applied to prosthesis 100 after exterior contacting portion 110 is produced with asymmetric force producing structures. Similarly, asymmetric biasing structures may be later added to a device having existing ingrowth structures.

In some cases, prosthesis 100 may be provided with mounting structure 115 which may be implemented in many ways and used as a mechanism to secure an external tool to prosthesis 100. In one case, structure 115 may include a solid structure attached at an apex of interior surface 120. That solid structure may further define an externally accessible cavity including threaded sidewalls. The external tool may include an extension having an exterior threaded surface complementary to the threaded sidewalls of structure 115.

In use, an operator may attach the external tool (an example is illustrated later in FIG. 8) to mounting structure 115 and begin to apply an inserting force prosthesis 100 into an installation site. That inserting force may be a non-impacting force applied by a BMD-type device as described in the incorporated patents and applications or it may be an impacting force applied by a mallet, hammer, or the like. Exterior contacting portion 110 may be configured so a net insertion-resisting force relative to the side walls of the installation is less than a net withdrawal-resisting force relative to the side walls. This arrangement may allow for decreased installation forces as opposed to a prosthesis having an outer surface with symmetric or randomized resisting forces. In some implementations, each incremental depth increase may be performed with less inserting force and each position may be thought of being anchored in place with a bias to increasing the installation depth responsive to forces applied to and by the external tool.

In some embodiments, when the asymmetric forces have enough differential, and when the installation site is prepared in an appropriate fashion, some embodiments may allow for insertion to result from generalized low-level vibration or periodic forces that bias prosthesis ever deeper into the installation site.

Figure 2:
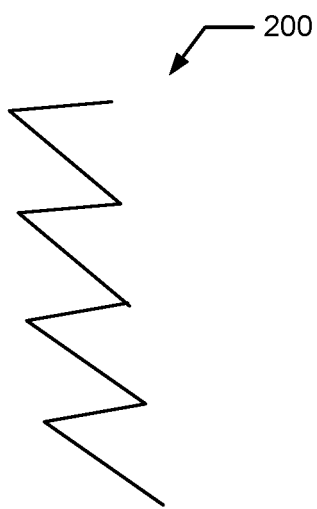
FIG. 2 illustrates a sectional side view of an embodiment of a surface treatment.
Figure 3:
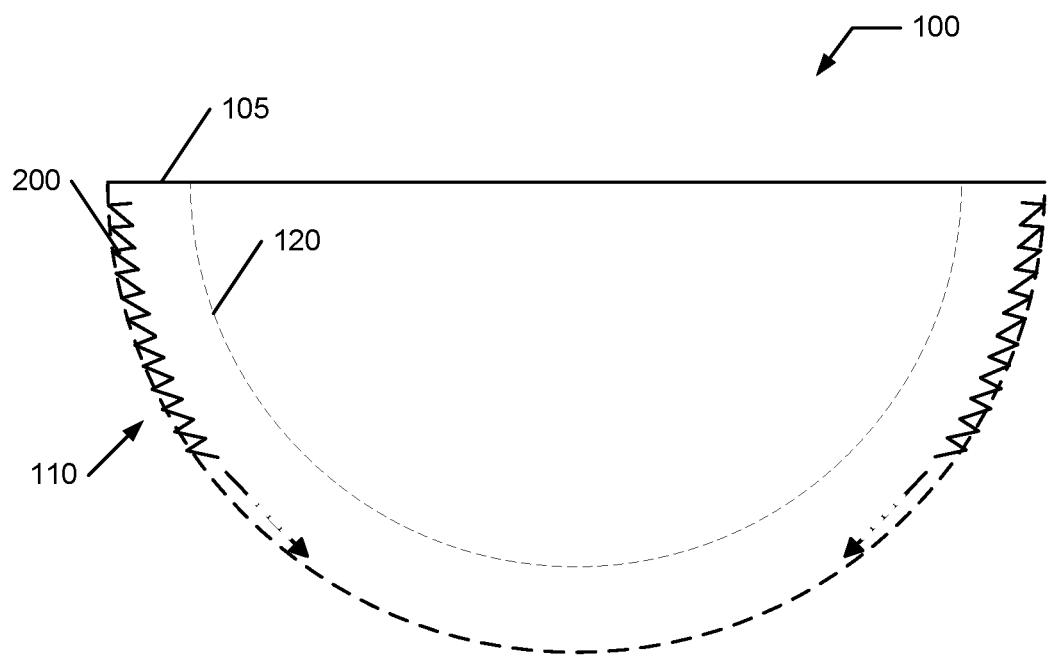
FIG. 3 illustrates a sectional side view of an embodiment of the surface treatment of FIG. 2 applied to a prosthesis of FIG. 1.

FIG. 2 illustrates a sectional side view of an embodiment of a surface treatment 200. Surface treatment 200 includes a series of asymmetric "steps" that may be included as all, or a portion of, exterior contacting portion 110, extending 360 degrees around foundation portion 105 when viewed from above. FIG. 3 illustrates a sectional side view of a surface treatment 200 included as part of prosthesis 100 as exterior contacting portion 110. In some embodiments, surface treatment 200 may not extend over an entire height of prosthesis 100. In some embodiments, surface treatment 200 may not include a regular step profile. The step profile of surface treatment 200 is representative of asymmetrically angled surface elements of the type that may be used for asymmetric resisting forces.

Figure 4:
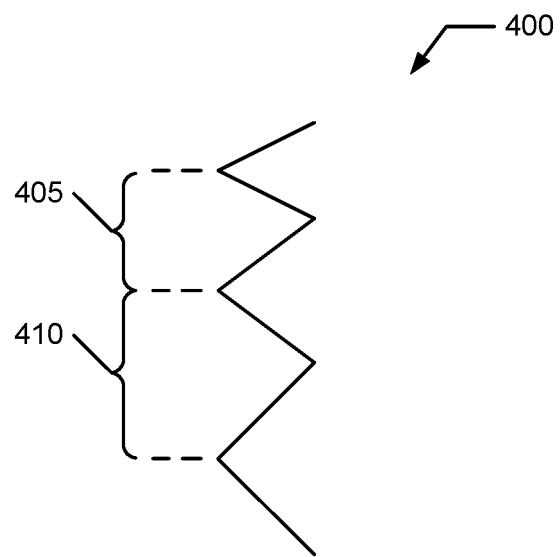
FIG. 4 illustrates a sectional side view of an alternative embodiment of a surface treatment.
Figure 5:
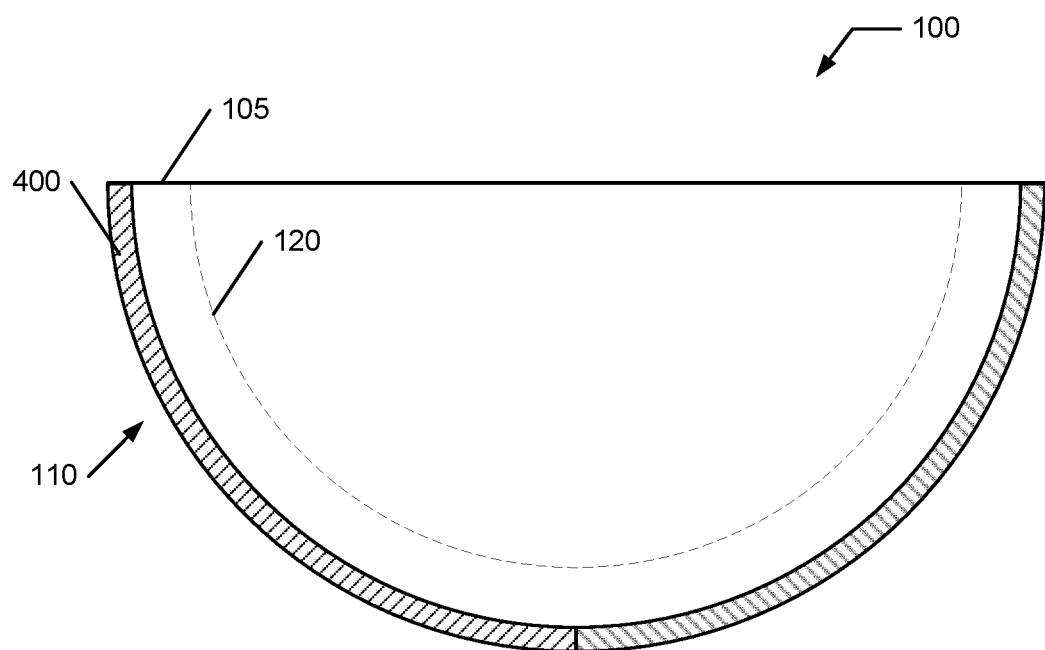
FIG. 5 illustrates a representative sectional side view of an embodiment of the alternative surface treatment of FIG. 4 applied to a prosthesis of FIG. 1.

FIG. 4 illustrates a sectional side view of an alternative embodiment of a surface treatment 400. Surface treatment 400 illustrates a concept of variable pitch in which a first distance 405 between a first set of adjacent peaks of surface treatment 400 is different than a second distance 410 between a second set of adjacent peaks of surface treatment 400. There are many different possible implementations for surface treatment 400. While surface treatment 400 is illustrated as having continuously variable distances between a pair of peaks, surface treatment 400 may also be implemented as having a first portion of substantially matching (or varying using a first variable peak profile) pitch distances and then having one or more additional portions, each portion including substantially matching (or varying using the same or additional variable peak profiles) pitch distances within its portion. That is to say, a top portion, perhaps a top quarter or a top third of prosthesis 100, for example, may include a first configuration for pitches as part of surface treatment 400 while a bottom portion, perhaps a bottom quarter or a bottom third of prosthesis 100, for example, may include a second configuration for pitches as part of surface treatment 400. FIG. 5 illustrates a representative sectional side view of surface treatment 400 included with prosthesis 100 as exterior contacting portion 110. The variable pitches may provide for asymmetric resisting forces. As illustrated, surface treatment 400 includes a generally symmetric peak pattern. In some embodiments, surface treatment 400 may include a modification of surface treatment 200 to include one or more regions of variably spaced "asymmetrically-angled peaks" when included as part of exterior contacting portion 110.

The distribution of these portions may be other than this example (top and bottom portions) and different regions and portions may have different expanses (e.g., a top third and a bottom quarter) for example. In other embodiments, exterior contacting portion 110 may include one or more regions of surface treatment 200 and one or more regions of surface treatment 400.

Figure 6:
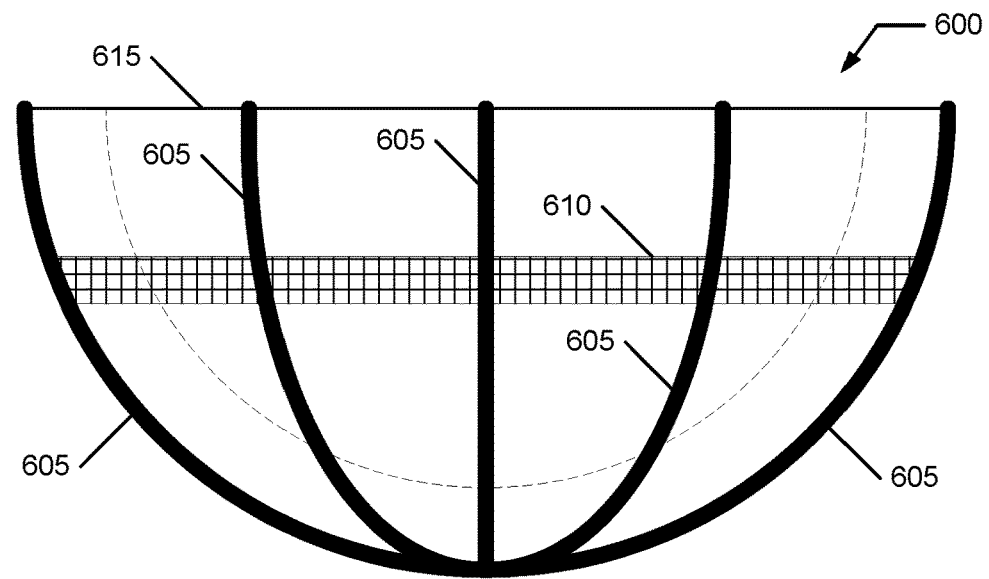
FIG. 6 illustrates a side view of a prosthesis including a two-dimensional asymmetrical stiffness.
Figure 7:
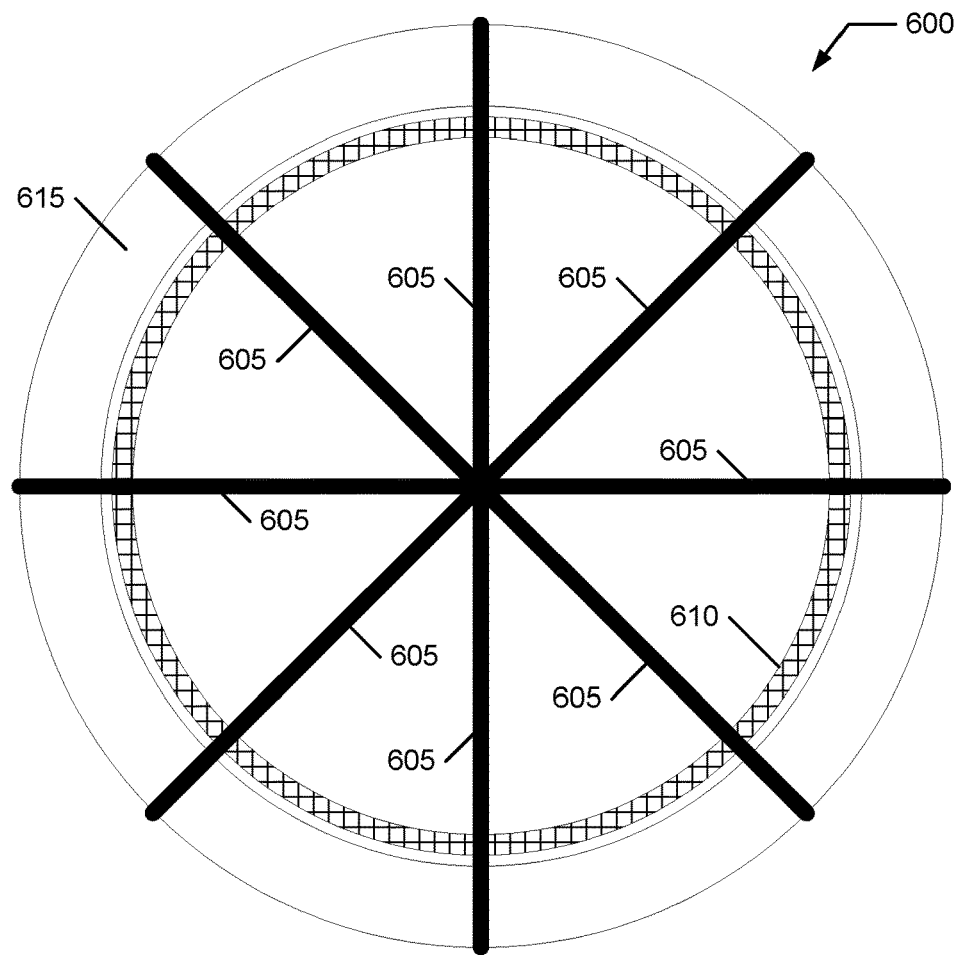
FIG. 7 illustrates a top view of the prosthesis of FIG. 6.

FIG. 6 illustrates a side view of a prosthesis 600 including a two-dimensional asymmetrical stiffness configuration, and FIG. 7 illustrates a top view of prosthesis 600. Prosthesis 600 includes a set of ribs 605 and one or more planks 610 disposed as part of a prosthetic body 615, represented as an alternative acetabular cup. Body 615 may be implemented in conventional fashion or may include an arrangement consistent with prosthesis 100. Ribs 605 and plank(s) 610 are configured to provide an asymmetric two-dimensional (2D) stiffness to body 615 that may be more conducive to transmission of force and energy through the longitudinal axis of the cup as opposed to circumferentially. Ribs 605 are longitudinally extending inserts within body 615 (and/or applied to one or more exterior surfaces of body 615). Plank(s) 610 is/are laterally extending circumferential band(s) within body 615 (and/or applied to one or more exterior surfaces of body 615). For example, planks 610 may be "stiffer" than ribs 605 (or vice-versa) to produce a desired asymmetric functional assembly that may provide for an undulatory body motion as it is installed into position.

The illustration of FIG. 6 is not to be understood as implying that the present invention requires that ribs and planks be maintained at relative right angles as illustrated. In some implementations, to achieve a desired affect or motion, other angular relationships between the ribs and planks are possible (e.g., 30, 45, 60-degree relationships, or more generally an angular (which may be constant or varying at different locations) range of 5-90 degrees.

An alternate implementation could include other arrangements of intersecting multidimensional (e.g., 2D or 3D structures) such as a pair of counter-cyclical helical structures implemented in a body of a prosthesis. That is, for a prosthesis having a particular axis, one structure is installed clockwise about that axis and another structure is installed counter-clockwise about that axis. The frequency of wrap, material type, tension, nature of integration, and other factors influence the asymmetric stiffness imparted by these structures that in turn may influence a resulting undulatory motion in response to forces moving the prosthesis along an installation path. In some cases, it may be desired to provide a particular undulation motion for removal rather than for installation as the present invention is not constrained to just improving installation of a prosthesis into a bone.

In some embodiments, a use of a tool, for example a BMD prototype, allows an operator to insert a prosthesis with more control and less force. Use of such a tool coupled with prosthesis 600 that has an asymmetrical "structural" and hence asymmetrical "functional" propensity for longitudinal seating, the operation may be able to be completed with less force, and thus more safely, efficiently, and/or accurately.

The acetabular cup and all implants in orthopedic surgery may benefit from various types of differentiation (where the structure of the implant in and by itself) enhances the functionality of the implant. Prosthesis 600 may alternatively, or in addition, include a "cross helical arrangement" of fibers, strands, cables, ropes, or other structures to be simulated on the surface of, or in the body of, prosthetic implants (e.g., acetabular cups) and hence the creation of "two-dimensional stiffness". The creation of "fiber angels" on the surface of the implant creates better and easier seating of the implant, with more efficient transmission of force from an insertional tool to the cup (implant) to the pelvic bone.

Prosthesis 600 may be referred to generally as an "intelligent prosthesis" and acetabular cup where the manipulation of the structure and surface of the implant significantly affects the functionality of the implant particularly during the actual surgery, this implant will have been fine-tuned functionally to insert. This cup through its inherent structural specifications discussed above will complement the use of BMD vibratory insertional tool (bidirectional or unidirectional versions). This concept may apply to many different orthopedic implants used for reconstruction and trauma, and other structures to be inserted or assembled together.

Figure 8:
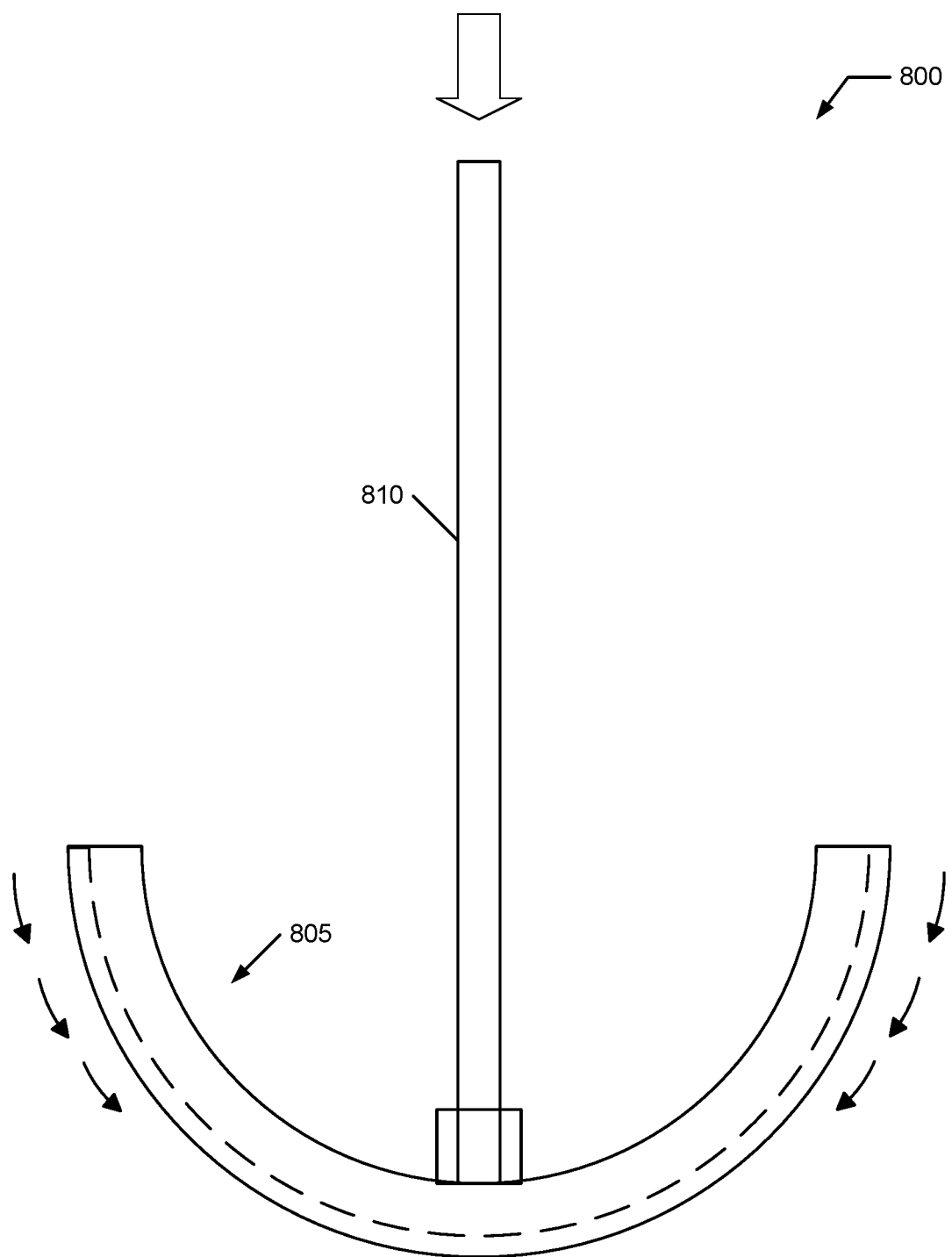
FIG. 8 illustrates a side view of a pulling of a prosthesis along an installation path responsive to an apex-attached force applicator.

FIG. 8 illustrates a side view of a system 800 pulling a prosthesis 805 along an installation path responsive to an apex-attached force applicator 810. In some cases, for a prosthesis having 2D functional asymmetry, it may be desirable or undesirable to pull prosthesis 805 in such as fashion depending upon the differing moduli of stiffness and arrangement of components. In some arrangements, it may be undesirable to pull prosthesis into position in the manner illustrated in FIG. 8.

Figure 9:
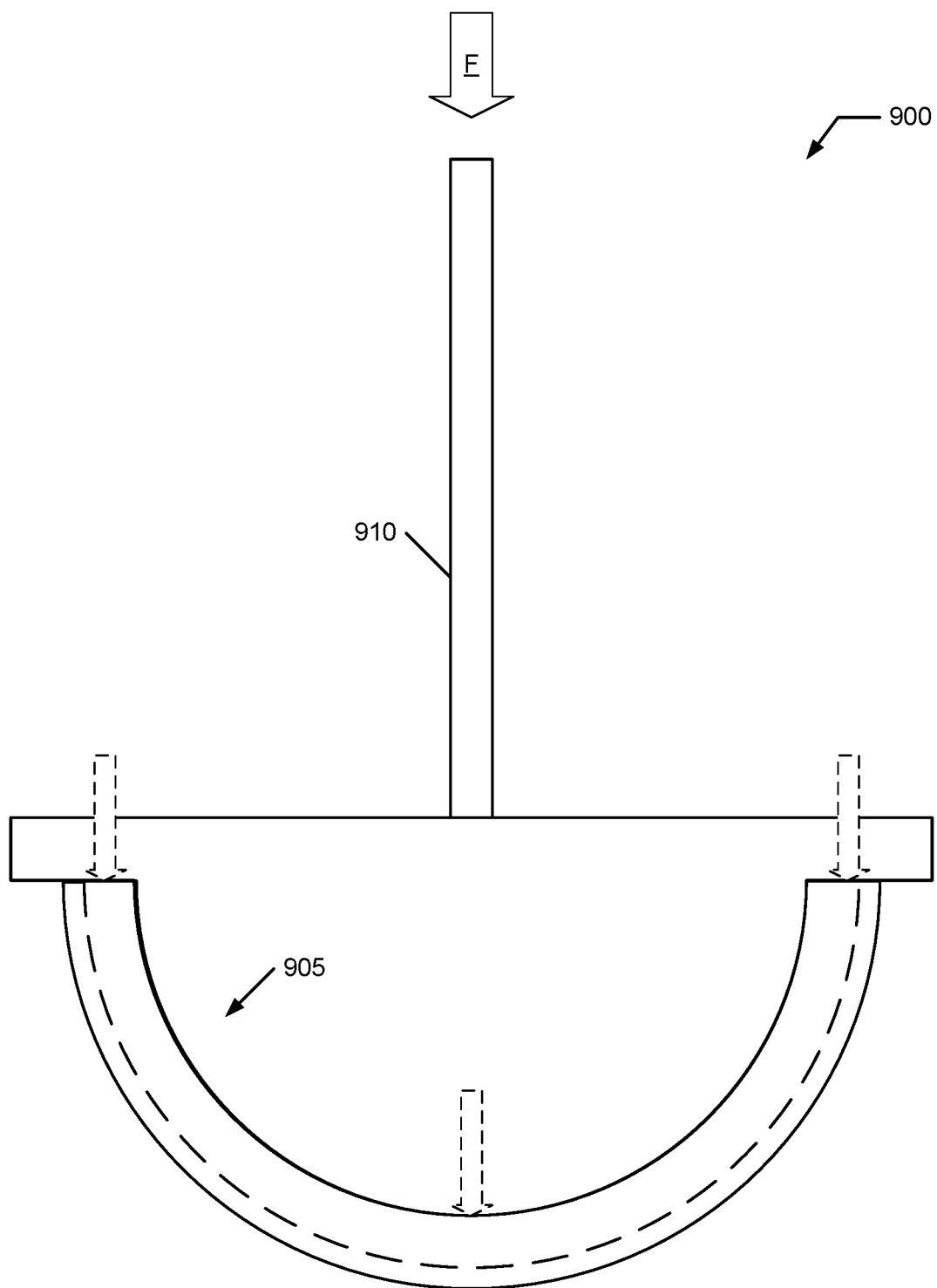
FIG. 9 illustrates a side view of a pushing of a prosthesis along an installation path responsive to a whole-surface interior adaptor force applicator.
Figure 10:
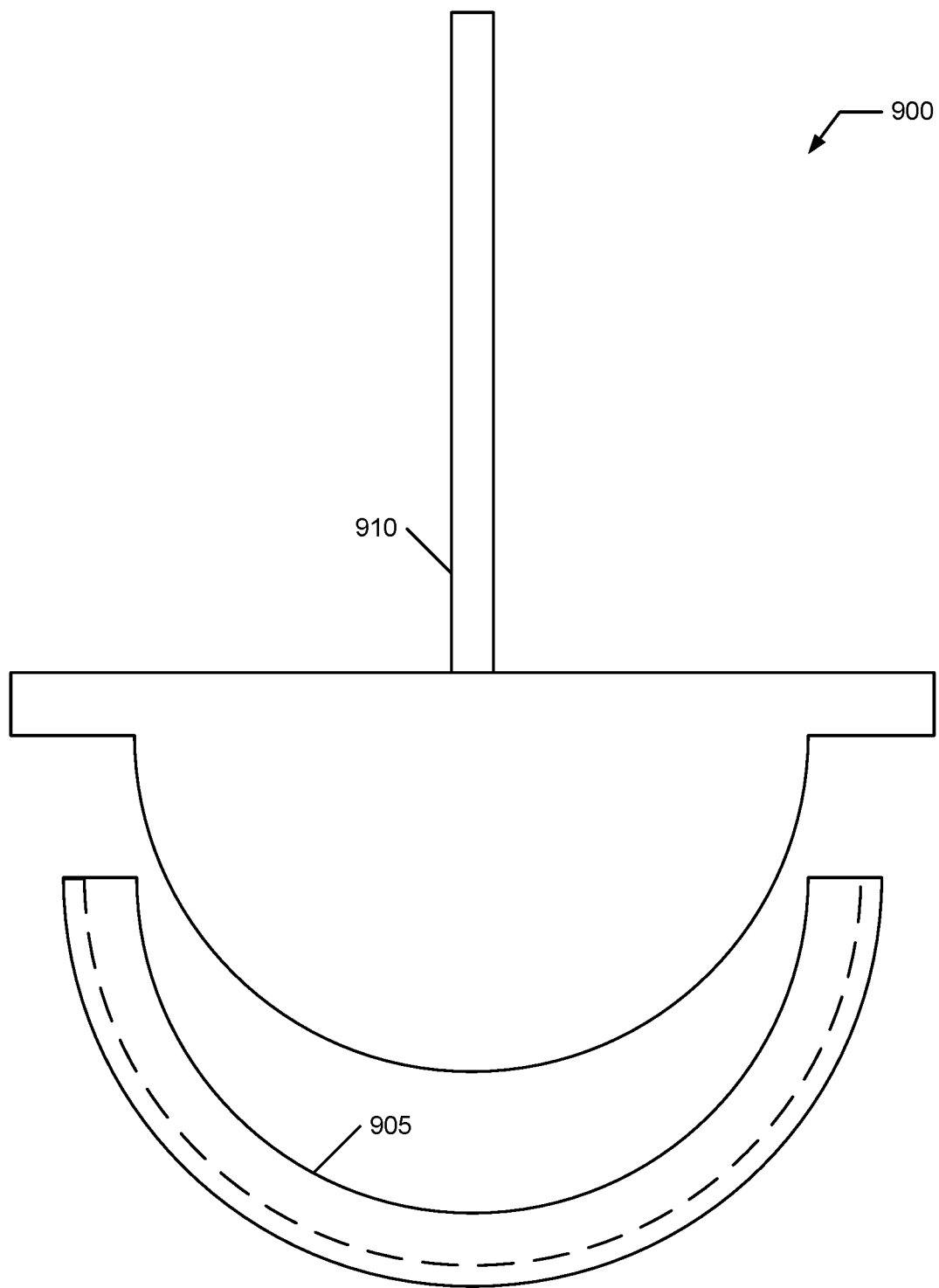
FIG. 10 illustrates a side view of the whole-surface interior adaptor force application disengaged from the prosthesis to better illustrate its configuration.

FIG. 9 illustrates a side view of a system 900 pushing of prosthesis 905 (e.g., prosthesis 600) along an installation path responsive to a whole-surface interior adaptor force applicator 910, and FIG. 10 illustrates a side view of system 900 with whole-surface interior adaptor force applicator 910 disengaged from prosthesis 905 to better illustrate its configuration. Applicator 910 sits into prosthesis 905 and "pushes" it down into position. In some embodiments may provide that "pushing" prosthesis 905 into position with applicator 910 (such as a BMD or a BMD-type device) possibly engages an undulatory motion of prosthesis 905 more effectively, such as in some cases when prosthesis 905 includes an embodiment of prosthesis 600 configured for undulation in response to an appropriate series longitudinal insertion forces F.

Figure 11:
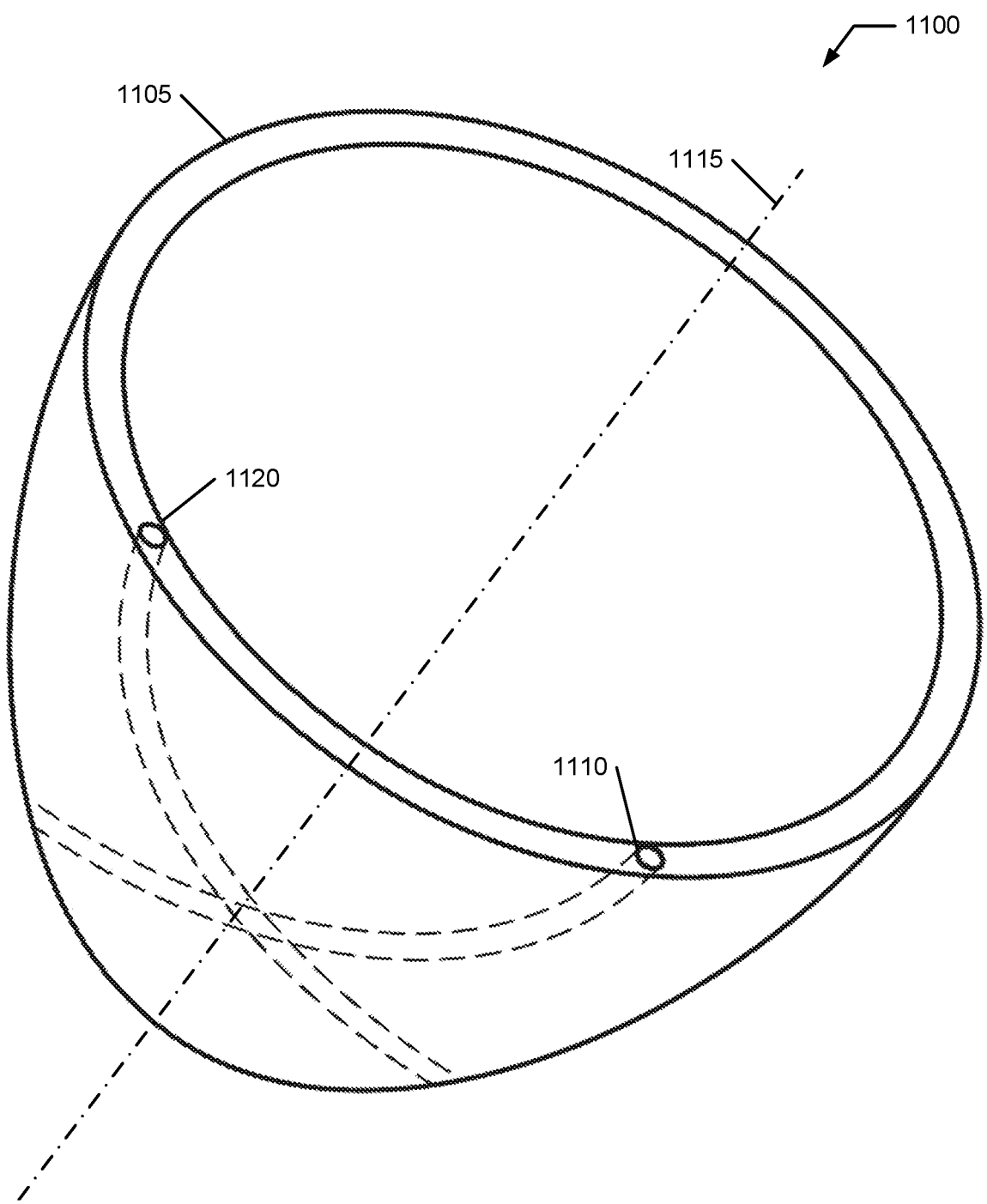
FIG. 11 illustrates perspective view of a prosthesis including a two-dimensional asymmetrical stiffness implemented by counter-rotational helical structures disposed within a foundation of the prosthesis.

FIG. 11 illustrates perspective view of a prosthesis 1100 including a two-dimensional asymmetrical stiffness implemented by counter-rotational helical structures disposed within a foundation 1105 of prosthesis 1100. Prosthesis 1100 includes a first set 1110 of helical structures installed clockwise about an axis 1115 and includes a second set 1120 of helical structures installed counterclockwise about axis 1115; the sets of helical structures cooperatively configured to produce a two-dimensional asymmetric stiffness implementing a bias for insertion of prosthesis 1100.

Another embodiment of the present invention may include a material applied alone or as part of another surface treatment to contacting surfaces of a prosthesis. This embodiment includes a completely novel idea for insertion of a prosthesis such as an acetabular cup. Depending upon context, there are materials that may significantly decrease relative friction between two contacting objects moving past each other. A use of a BMD vibrational tool may help to facilitate the use of similar concept. An embodiment may include a bio-absorbable or bio-degradable material (e.g., a paste, cream, gel, or other substance) configured for use during the insertion process, e.g., of an acetabular cup into the acetabulum, to decrease the relative forces between contacting surfaces at the cup and bone interface. For example, this material could be an antibiotic paste that absorbs immediately after insertion, or a rapidly dissolving paste such as calcium hydroxylapatite (HA) [Ca10(OH)2 (PO4)6], Beta tricalcium phosphate, an HA/B TCP combination; all of which can be made into paste and slurries that dissolve over controlled amounts of time. An embodiment of the present invention may include use of a surface-applied material (such as a cream, gel, paste or the like) to minimize relative forces during the insertion/assembly of an implant with a tool, such as the BMD prototype or other installation tool. Of course, this idea applies to other implants, for example those that require the use of force and that would benefit from the BMD vibrational insertion tool, as well as other procedures and tools.

Surface treatment and/or application of a surface material may reduce installation forces. One possible theory is that the surface treatment and/or surface material manipulates of the applicable friction coefficients through shifting a contribution from static to kinetic coefficients as well as reducing the applicable static and/or kinetic coefficient. For a surface treatment such as a paste, slurry, ice, or the like, such manipulation may be temporary during the time that the prosthesis is installed. Thereafter the values for the coefficients may revert to the previous, unaltered values. This may be used to advantage in helping to improve the retentive forces holding the prosthesis in place after installation.

Described herein is use of a paste or slurry that absorbs over time after installation (in some cases quickly such as ice) after the insertion (HA) [Ca10(OH)2 (PO4)6], Beta tricalcium phosphate, and HA/B TCP combination, all of which may be made into a paste and/or a slurry that can be applied to the surface of the cup and dissolve over a controlled period of time, preferably immediately after the insertion of the cup is complete. In addition, there is another concept that uses a more simple and ubiquitous phenomena to reduce installation forces (e.g., possibly to reduce the applicable coefficients of friction), to allow easier insertion of the acetabular prosthesis into the acetabulum. That is to create a simple method of freezing sterile water on the cup and within the porous coating surface of the cup to provide a full or partial ice film at the juncture of the cup and the bone of the installation site. The porous coating comprises of microstructural features such as peaks, valleys and deep caves. In one sense, this structure may mimic the structure of trabecular/cancellous bone with its three-dimensional and interconnecting network of pores and capillary properties. The porous coating aids in initial scratch fixation as well as long term fixation through osseointegration of bone with its surface. Recently, there have been many advances in the creation of the porous coating that more accurately resemble the trabecular bone. Filling these gaps with sterile ice water that is then frozen is expected to dramatically decrease the applicable installation forces (possibly by reducing the applicable coefficients of friction) and hence FR (resistive force for insertion of a cup into a cavity). This method of using ice water is ideal in that as soon as the cup is exposed to the body fluids the ice will melt returning the coefficient of static friction (for the cup/cavity interface) to its original value before the application of ice. In this manner whether a biological paste, antibiotic paste, or ice is utilized, the coefficient of static friction may be temporarily (disarmed) so that easy insertion can occur. All these methods whether they rely on the paste, slurry or ice perform the same function to temporarily diminish the FR or applicable resistive force(s) for the cup/cavity interaction, and resolve shortly after insertion, and thereby return the relative forces to unaltered values—except that after installation these resistive now resist removal in contrast to resisting installation. This is akin to "tricking" the body to open a short window of time to allow easy insertion of a prosthesis. This is a new and novel method that can be utilized to make acetabular cup insertion easier with any insertion tool or method, including with the disclosed and incorporated devices, systems, and methods.

The system and methods above have been described in general terms as an aid to understanding details of preferred embodiments of the present invention. In the description herein, numerous specific details are provided, such as examples of components and/or methods, to provide a thorough understanding of embodiments of the present invention. Some features and benefits of the present invention are realized in such modes and are not required in every case. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

It will also be appreciated that one or more of the elements depicted in the drawings/figures can also be implemented in a more separated or integrated manner, or even removed or rendered as inoperable in certain cases, as is useful in accordance with a particular application.

Additionally, any signal arrows in the drawings/Figures should be considered only as exemplary, and not limiting, unless otherwise specifically noted. Combinations of components or steps will also be considered as being noted, where terminology is foreseen as rendering the ability to separate or combine is unclear.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed as new and desired to be protected by Letters Patent of the United States is:

1. A method for producing a prosthesis for an installation of the prosthesis into a cavity preconfigured for a press fit fixation of the prosthesis, comprising:
   a) manufacturing additively a structure for the prosthesis, said structure including a foundation and a surface; and
   b) during said manufacturing step a) establishing one or more portions of said structure configured to produce a structural surface asymmetry between said one or more portions of said structure and the preconfigured cavity during the installation, said structural surface asymmetry including a set of exterior surface structures that extend, relative to an insertion path, that include a pitch having a monotonic varying spacing between adjacent peaks, said pitch; and
   wherein each said peak includes a symmetric peak angle.

2. The method of claim 1 wherein said monotonic varying spacing increases while extending from a rim of the prosthesis to an apex of the prosthesis.

3. The method of claim 1 wherein said monotonic varying spacing decreases while extending from a rim of the prosthesis to an apex of the prosthesis.

4. The method of claim 2 wherein a pitch spacing change of said monotonic varying spacing is uniform.

5. The method of claim 3 wherein a pitch spacing change of said monotonic varying spacing is uniform.

6. The method of claim 1 wherein said surface includes a plurality of regions, with said exterior surface structures of each particular region have a pitch spacing profile between adjacent peaks matching other said pitch spacing profiles of other pairs of adjacent peaks within said particular region.

7. The method of claim 6 wherein said pitch spacing profile includes a constant pitch spacing for said adjacent peaks within each said region.

* * * * *